(12) United States Patent
Benchikh et al.

(10) Patent No.: US 10,539,557 B2
(45) Date of Patent: Jan. 21, 2020

(54) AH-7921 DETECTION

(71) Applicant: Randox Laboratories Ltd., Crumlin (GB)

(72) Inventors: Elouard Benchikh, Crumlin (GB); Ivan McConnell, Crumlin (GB); Peter FitzGerald, Crumlin (GB); Philip Lowry, Crumlin (GB)

(73) Assignee: Randox Laboratories Ltd., Crumlin (GB)

( * ) Notice: Subject to any disclaimer, the term of this patent is extended or adjusted under 35 U.S.C. 154(b) by 324 days.

(21) Appl. No.: 15/042,095

(22) Filed: Feb. 11, 2016

(65) Prior Publication Data
US 2016/0245800 A1    Aug. 25, 2016

(30) Foreign Application Priority Data
Feb. 11, 2015  (GB) .................................. 1502226.2

(51) Int. Cl.
*G01N 33/53* (2006.01)
*C07K 16/44* (2006.01)

(52) U.S. Cl.
CPC ......... *G01N 33/5308* (2013.01); *C07K 16/44* (2013.01); *C07K 2317/14* (2013.01); *C07K 2317/33* (2013.01); *C07K 2317/92* (2013.01)

(58) Field of Classification Search
CPC ........................... C07K 16/44; C07K 2317/14; C07K 2317/33; C07K 2317/92; G01N 33/5308
See application file for complete search history.

(56) References Cited

U.S. PATENT DOCUMENTS

2003/0224447 A1* 12/2003 McConnell ............ C07K 16/44
                                                           435/7.1

FOREIGN PATENT DOCUMENTS

EP         2716659 A1    4/2014

OTHER PUBLICATIONS

Szurdoki et al., "Important Factors in Hapten Design and Enzyme-Linked Immunosorbent Assay Development," in Immunoanalysis of Agrochemicals; Nelson, J., et al.; ACS Symposium Series, 1995, vol. 586, Chapter 4, pp. 39-63.*
Peterson et al., "Using hapten design to discover therapeutic monoclonal antibodies for treating methamphetamine abuse," J. Pharmacol. Exp. Ther., Jul. 2007; vol. 322, No. 1, pp. 30-39. Epub Apr. 23, 2007.*
Englebienne, "Immune and Receptor Assays in Theory and Practice," CRC Press, 2000, p. 308.*
Richard A. Goldsby, "Immunology," Macmillan, Nov. 29, 2002, p. 69.*
Scott-Moncrief et al., "Evaluation of antithyroglobulin antibodies after routine vaccination in pat and research dogs," J. Am. Vet. Med., 2002, vol. 221, No. 4, p. 499.*
Goodrow et al., "Strategies for Immunoassay Hapten Design," in Immunoanalysis of Agrochemicals; Nelson, J., et al.; ACS Symposium Series, 1995, vol. 586, Chapter 9, pp. 119-139.*
Kronstrand R. et al., "Fatal Intoxications Associated with the Designer Opioid AH-7921," Journal of Analytical Toxicology 2014; 38: 599-604.
Wohlfarth A. et al., "AH-7921, A Designer Synthetic Opioid: In Silico Prediction, Metabolic Stability Assessment with Human Liver Microsomes, Human Hepatocyte Metabolite Identification by High-Resolution Mass Spectrometry and Confirmation in an Authentic Urine Specimen," Oral Presentation at TIAFT Conference Buenos Aires, 2014.
Vorce S.P. et al., "A Fatality Involving AH-7921," Journal of Analytical Toxicology, vol. 38, No. 4, pp. 226-230 (2014).
Crawley D. "Development of the First Polyclonal Antibody for thee Detection of the Synthetic Opiod AH-7921 and Its Main Metabolite Nor-AH-7921 Poster 49," 53rd TIAFT Meeting 2015 Firenze, Aug. 30, 2015, p. 148.
Geneva: World Health Organization, "AH-7921 Critical Review Report Agenda item 4.21 Expert Committee on Drug Dependence Thirty-sixth Meeting," Jun. 16, 2014.
EP 16 154 935; European Search Report dated Jun. 1, 2016.

* cited by examiner

*Primary Examiner* — Galina M. Yakovleva
(74) *Attorney, Agent, or Firm* — Womble Bond Dickinson (US) LLP

(57) ABSTRACT

Antibodies, immunoassay methods and kits for the detection and determination of 3,4-dichloro-N-[(1-(dimethylamino) cyclohexyl)methyl]benzamide and 3,4-dichloro-N-[(1-(methylamino)cyclohexyl)methyl]benzamide, as well as the precursory immunogens, are described.

11 Claims, No Drawings

AH-7921 DETECTION

CROSS REFERENCE TO RELATED APPLICATIONS

The instant application claims the benefit of priority under 35 USC § 119 to United Kingdom Application No. 1502226.2, entitled "AH-7921 Detection" filed 11 Feb. 2015, the entire contents of which are incorporated herein by reference in their entirety.

BACKGROUND OF THE DISCLOSURE 3,4-Dichloro-N-[(1-(dimethylamino)cyclohexyl)methyl]benzamide, commonly known as AH-7921, is a psychoactive synthetic drug of the opioid class. Pharmacologically similar to morphine, it has a high addictive potential and has been implicated in a number of deaths—hence the clinical and forensic toxicological need for its detection (EMCDDA (2014)—Europol Joint Report on a new psychoactive substance: AH-7921 3,4-dichloro-N-{[1-(dimethylamino)-cyclohexyl]methyl}benzamide ISSN 1977-7868). The pharmacokinetic profile of this compound based on animal, in vitro, in silico and post-mortem analysis suggests that the main metabolic pathway involves demethylation to nor-AH-7921 or 3,4-dichloro-N-[(1-(methylamino)cyclohexyl)methyl]benzamide (Kronstand et al., 2014; Wohlfarth et al., 2014 *J. Anal. Toxicol.*, 28: 599-604). To date detection of the parent drug and metabolites has been effected using laboratory-based mass-spectrometry (e.g. Kronstand et al., 2014, ODA7, Conference Abstract, TIAFT, Argentina), the equipment for which is expensive and requires highly-trained operators.

SUMMARY OF THE DISCLOSURE

Described herein is an immunoassay for the selective detection and determination of 3,4-dichloro-N-[(1-(dimethylamino)cyclohexyl)methyl]benzamide and 3,4-dichloro-N-[(1-(methylamino)cyclohexyl)methyl]benzamide. The immunoassay is underpinned by novel and highly sensitive antibodies. Also described are novel immunogens, and substrates and kits incorporating antibodies of the invention.

In one aspect disclosed herein is an immunogen of the structure:

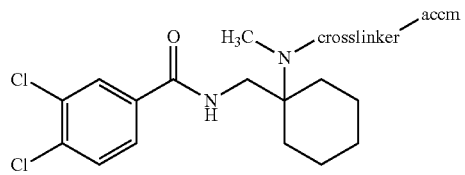

wherein, the accm is an antigenicity conferring carrier material.

In a further aspect disclosed is an antibody raisable against an immunogen of the present invention.

In a yet further aspect disclosed is a method of detecting or determining 3,4-dichloro-N-[(1-(dimethylamino)cyclohexyl)methyl]benzamide or 3,4-dichloro-N-[(1-(methylamino)cyclohexyl)methyl]benzamide in a sample comprising i) contacting the sample with a detecting agent and an antibody of the present invention; and ii) detecting or determining the amount of detecting agent bound to the antibody.

In a still further aspect disclosed herein is a kit comprising a disclosed antibody.

In a yet still further aspect disclosed herein is the immunogen wherein the crosslinker is —X—Y—, in which X is a substituted or unsubstituted, straight or branched chain, saturated or unsaturated alkylene moiety and Y, attached to the antigenicity conferring carrier material, is selected from the group consisting of —C(O)—, —NH—, —N(R)— in which R is C1-6 alkyl chain, maleimido, ester, thioester, amido, thioamido, sulphoxide, sulphonyl or a dithiopyridylene moiety.

In a yet still further aspect disclosed herein is the immunogen wherein X is —(CH2)$_n$—C(O)— and n=1-6.

In a yet still further aspect disclosed herein is the immunogen wherein X is —CH2—CH2—CH$_2$— and Y is —C(O)—.

In a yet still further aspect disclosed herein are antibodies raised to an immunogen of any of the disclosed compounds.

In a yet still further aspect disclosed herein are antibodies further characterised in having a cross-reactivity of 100% to 3,4-dichloro-N-[(1-(dimethylamino)cyclohexyl)methyl]-benzamide and a cross-reactivity of >20% to 3,4-dichloro-N-[(1-(methylamino)cyclohexyl)-methyl]benzamide.

In a yet still further aspect disclosed herein are antibodies of further characterised in having a cross-reactivity of 100% to 3,4-dichloro-N-[(1-(dimethylamino)cyclohexyl)methyl]-benzamide and a cross-reactivity of >50% to 3,4-dichloro-N-[(1-(methylamino)cyclohexyl)-methyl]benzamide.

In a yet still further aspect disclosed herein are antibodies having a cross-reactivity of 100% to 3,4-dichloro-N-[(1-(dimethylamino)cyclohexyl)methyl]benzamide and a cross-reactivity of >20% and <100% to 3,4-dichloro-N-[(1-(methylamino)cyclohexyl)methyl]-benzamide.

In a yet still further aspect disclosed herein are antibodies having a cross-reactivity of 100% to 3,4-dichloro-N-[(1-(dimethylamino)-cyclohexyl)methyl]benzamide and a cross-reactivity of >50% and <100% to 3,4-dichloro-N-[(1-(methylamino)cyclohexyl)methyl]-benzamide.

In a yet still further aspect disclosed herein are antibodies having an IC50 of <1.00 ng/mL to each of 3,4-dichloro-N-[(1-(dimethylamino)-cyclohexyl)methyl]benzamide and 3,4-dichloro-N-[(1-(methylamino)cyclohexyl)-methyl]benzamide.

In a yet another further aspect disclosed herein is an immunoassay method of detecting or determining 3,4-dichloro-N-[(1-(dimethylamino)cyclohexyl)methyl]benzamide and 3,4-dichloro-N-[(1-(methylamino)cyclohexyl)methyl]benzamide in a solution or an in vitro sample taken from an individual with one or more detecting agents and a disclosed antibody; measuring the signal or signals produced by the one or more detecting agents; and deducing the presence of, or amount of, 3,4-dichloro-N-[(1-(dimethylamino)cyclohexyl)-methyl]benzamide and 3,4-dichloro-N-[(1-(methylamino)cyclohexyl)methyl]benzamide.

DETAILED DESCRIPTION

In a first aspect, the invention is an immunogen of the structure:

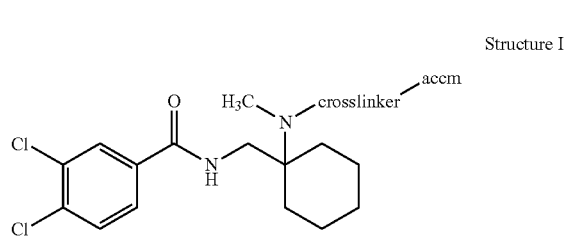

Structure I wherein the accm is an antigenicity conferring carrier material. Appropriate accms commonly contain poly(amino acid) segments and include polypeptides, proteins and protein fragments. Illustrative examples of antigencity conferring carrier materials are keyhole limpet haemocyanin (KLH), bovine thyroglobulin (BTG), bovine serum albumin (BSA), egg ovalbumin, bovine gamma globulin or cationised BSA. Alternatively, synthetic poly(amino acids) having a sufficient number of available amino groups, such as lysine, may be employed, as may other synthetic or natural polymeric materials bearing reactive functional groups. Also, carbohydrates, yeasts or polysaccharides may be conjugated to a hapten to produce an immunogen. The accm of the invention is preferably chosen from KLH, BTG, BSA or egg ovalbumin. To form the immunogen the accm is attached to a molecule which incorporates the epitopic target; this is achieved using a crosslinker (a functionalised spacing and linking group).

The crosslinker is standard in the field of antibody production (see below) and, like the accm, can be varied in the immunogen without undermining the binding characteristics of the subsequently produced antibody. The crosslinker may be any conventional cross linking group conventionally used in this field. The crosslinker is ideally a functionalised linking group joining the accm to a hapten. The term "crosslinker" as used herein is any bifunctional molecule able to covalently join the hapten element to an immunogenicity conferring carrier material. A suitable crosslinker to link with alternative carrier materials is maleimide, or a maleimide derivative, for example when BTG-maleimide is used to conjugate with the hapten via a cysteine residue. Other crosslinkers which could also couple this group on the cysteine include haloacetyls and pyridyldisulfides. Either Lys residue, or the Glu residue (C-terminal) may alternatively be used to conjugate to a carrier material, optionally via a cross-linking group, to form an immunogen. For example, a primary amine group on the side chain of lysine (Lys) could be coupled using a crosslinker selected from N-hydroxysuccinimide esters, imidoesters, PFP esters or hydroxymethyl phosphine. As another example, glutamic acid (Glu) could be coupled using a carbodiimide crosslinker: 1-Ethyl-3-(3-dimethylaminopropyl)-carbodiimide EDC or N,N'-Dicyclohexylcarbodiimide (DCC). In one embodiment, the crosslinker may comprise or consist of a carboxyl, dithiopyridyl, maleimidyl, amino, hydroxyl, thiol and aldehyde moiety. The crosslinker is well known to the skilled person in immunogen synthesis.

The crosslinker of Structure I is preferably —X—Y—, in which X is a substituted or unsubstituted, straight or branched chain, saturated or unsaturated alkylene moiety preferably of chain length $C_{1-10}$, more preferably $C_{1-6}$ and Y is a functional group attached to the antigenicity conferring carrier material.

The term "functional group" is a standard phrase in the chemistry field and refers to a reactive group such as an amine, ketone, ether, thioether, amide, alkene, thiol, ester, carboxylic acid or aldehyde. An example of a crosslinker is 4-N-maleimidomethylcyclohexyl-1-carboxylic acid NHS ester solution (available from Sigma-Aldrich). An alternative crosslinker which can be used to couple to haptens possessing a carboxylic acid is EDC and either sulfo-NHS (N-hydroxysulfosuccinimide) or homocysteinethiolactone, all of which are known in the art and are commercially available.

In one embodiment, Y is selected from the group consisting of carbonyl i.e. —C(O)—, —NH—, —N(R)— in which R is $C_{1-6}$ alkyl chain, maleimido, ester, thioester, amido, thioamido, sulphoxide, sulphonyl or a dithiopyridylene moiety. In one embodiment, Y is —C(O)—, —NH—, —C(O)—NH—, —C=, or —S—. In one embodiment when the crosslinker of Structure I is —X—Y—, X is —$(CH_2)_n$— in which n is 1-6; a specific example is where —X— is —$CH_2$—$CH_2$—$CH_2$— and Y is —C(O)—.

The term "hapten" as used herein describes a pre-immunogenic molecule that stimulates antibody production only when linked to a larger carrier molecule. For the purposes of this patent application, "linked" is synonymous with bound, attached, conjugated, crosslinked, coupled, or chemically synthesised to. This larger carrier molecule can be referred to as an antigenicity-conferring carrier material (accm). Once the hapten is linked to the accm, it forms the immunogen.

As described herein, compounds of the invention may optionally be substituted with one or more substituents, such as illustrated generally below, or as exemplified by particular species of the invention. It will be appreciated that the phrase "optionally substituted" is used interchangeably with the phrase "substituted or unsubstituted." In general, the term "substituted", whether preceded by the term "optionally" or not, refers to the replacement of one or more hydrogen radicals in a given structure with the radical of a specified substituent. Unless otherwise indicated, an optionally substituted group may have a substituent at each substitutable position of the group. When more than one position in a given structure can be substituted with more than one substituent selected from a specified group, the substituent may be either the same or different at each position. When the term "optionally substituted" precedes a list, said term refers to all of the subsequent substitutable groups in that list.

Selection of substituents and combinations of substituents envisioned by this invention are those that result in the formation of stable or chemically feasible compounds. The term "stable", as used herein, refers to compounds that are not substantially altered when subjected to conditions to allow for their production, detection, and, specifically, their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week. Only those choices and combinations of substituents that result in a stable structure are contemplated. Such choices and combinations will be apparent to those of ordinary skill in the art and may be determined without undue experimentation.

The term "alkyl" as used herein means a saturated straight or branched chain hydrocarbon.

The term "alkylene," as used herein, represents a saturated divalent straight or branched chain hydrocarbon group and is exemplified by methylene, ethylene, isopropylene and the like.

Suitable substituents on a saturated carbon of an alkyl, aryl, cycloalkyl, or heterocyclic ring are $C_1$-$C_6$ alkyl, halogen, cyano, oxo, —NCO, —ORb, —$SR^b$, —$S(O)R^a$, —$SO_2Ra$, —$NR^bR^c$, —$C(O)R^b$, —$C(O)OR^b$, —$OC(O)R^b$, —$NRC(O)R^b$, —$C(O)NR^bR^c$, —$NR^bC(O)NR^bR^c$, —$NR^bC(O)OR^b$, —$OCONR^bR^c$, —$C(O)NRCO_2R^b$, —$NR^bC(O)NR^bC(O)OR^b$, —$C(O)NR(OR^b)$, —$SO_2NR^cR^b$, —$NR^bSO_2R^b$, —$NR^bSO_2NR^cR^b$, or —$P(O)(OR^a)_2$—; or two substituents join together with the atoms to which they are attached to form a 5-7-membered cycloalkyl or heterocyclic ring. Each $R^a$, $R^b$ and $R^c$ are each independently —H or $C_1$-$C_6$ alkyl. Other suitable substituents for a saturated carbon of an alkyl include the following: =O, =S, =NNHR*, =NN(R*)$_2$, =NNHC(O)R*, =NNHCO$_2$(alkyl), =NNHSO$_2$(alkyl), or =NR*, wherein each R* is independently selected from —H or $C_1$-$C_6$ alkyl.

Unless otherwise indicated, structures depicted herein are also meant to include all isomeric (e.g., enantiomeric, diastereomeric, cis-trans, conformational, and rotational) forms of the structure. For example, the R and S configurations for each asymmetric center, (Z) and (E) double bond isomers, and (Z) and (E) conformational isomers are included in this invention, unless only one of the isomers is drawn specifically. As would be understood to one skilled in the art, a substituent can freely rotate around any rotatable bonds. Therefore, single stereochemical isomers as well as enantiomeric, diastereomeric, cis/trans, conformational, and rotational mixtures of the present compounds are within the scope of the invention.

Unless otherwise indicated, all tautomeric forms of the compounds of the invention are within the scope of the invention.

Additionally, unless otherwise indicated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays. Such compounds, especially deuterium analogues, can also be therapeutically useful.

The compounds of the invention are defined herein by their chemical structures and/or chemical names. Where a compound is referred to by both a chemical structure and a chemical name, and the chemical structure and chemical name conflict, the chemical structure is determinative of the compound's identity.

A further aspect of the invention describes antibodies raisable from any of the immunogens described in the previous paragraph. A further aspect of the invention describes antibodies raised from any of the immunogens described in the previous paragraph.

The term "antibody" as used herein refers to an immunoglobulin or immunoglobulin-like molecule. In a one embodiment, the antibodies are polyclonal antibodies. However, the skilled person will understand that any type of immunoglobulin molecule or fragment thereof can be used, for example monoclonal antibodies, Fab fragments, scFv fragments and any other antigen binding fragments all of which fall within the scope of the current invention. The polyclonal antibodies may be produced by any method as known to those skilled in the art. Any suitable host animal may be used in the immunisation process including a mammalian animal for example, but not limited to, sheep, rabbit, mouse, guinea pig or horse. In addition, the antibodies may be in the form of polyclonal antisera.

The term "raisable" means that the antibody can be raised from an immunogen of the second aspect of the current invention but is not necessarily so raised. In this context, "raisable" includes, but is not limited to, "raised".

When used in reference to an antibody, the word "specific", "specifically" or "specificity" in the context of the current invention refers to the analyte or analytes that are bound by the antibody, as gauged by a suitable metric such as the sensitivity and cross-reactivity.

The phrase "an antibody which binds or specifically binds to an epitope of structure . . ." implies that the antibody, if polyclonal, will comprise clones whose high concentration and binding characteristics ensure an assay incorporating the antibody will bind to and ultimately support the identification of the compound of interest. Alternatively, the antibody could be a monoclonal antibody specific for a particular structural part of or the whole of the compound. There are several parameters that can be used to compare the relative degree of binding to an antibody of different analytes including the lowest limit of detection, the lowest limit of quantification and the $IC_{50}$. The $IC_{50}$ can be determined using a competitive assay and can be used to derive analyte cross-reactivities.

The terms "binds", "able to bind to" or "capable of binding" as used herein means that under standard immunoassay conditions, for example as described in 'Immunoassay: A practical guide' by Brian Law, Taylor and Francis Ltd (ISBN 0-203-48349-9), the antibodies will bind to said molecules.

For purposes of comparison, one analyte with high cross-reactivity is generally given a value of 100%, with all other analytes accorded a value relative to this; in addition, as is known by one skilled in the art, for cross-reactivity to be of practical use the analyte specific antibody must display a high sensitivity as measured by a suitable metric such as the $IC_{50}$. The $IC_{50}$ is a commonly used indicator of antibody sensitivity for immunoassays. To enable an assay to be effectively applied in the field, an $IC_{50}$ of less than or about 0.5 ng/ml, less than or about 0.250 ng/ml, less than or about 0.15 ng/ml, and or less than about 0.1 ng/mL for any individual analyte. Given the $IC_{50}$ of various analytes, their cross-reactivities, often represented as relative percentages, can be calculated.

Preferably the antibodies have a cross-reactivity of 100% to 3,4-dichloro-N-[(1-(dimethylamino)cyclohexyl)methyl]benzamide and a cross-reactivity of >20%, >50%, or >80% to 3,4-dichloro-N-[(1-(methylamino)cyclohexyl)-methyl]benzamide; in a preferred embodiment the antibodies have a cross-reactivity of 100% to 3,4-dichloro-N-[(1-(dimethylamino)cyclohexyl)methyl]benzamide and a cross-reactivity of >20% and <100%, >50% and <100%, or >80% and <100%, to 3,4-dichloro-N-[(1-(methylamino)cyclohexyl)-methyl]benzamide.

In addition to or independently of these cross-reactivity profiles, it is preferable that the antibodies have an $IC_{50}$ of <1.00 ng/mL to each of 3,4-dichloro-N-[(1-(dimethylamino)-cyclohexyl)methyl]benzamide and 3,4-dichloro-N-[(1-(methylamino)cyclohexyl)-methyl]benzamide; more preferably the $IC_{50}$'s of the antibodies are <0.10 ng/mL to each of 3,4-dichloro-N-[(1-(dimethylamino)cyclohexyl)methyl]-benzamide and 3,4-dichloro-N-[(1-(methylamino)cyclohexyl)methyl]benzamide. The sensitivities of the antibodies can be measured by any suitable metric used in the art such as the limit of detection, limit of quantitation as well as the $IC_{50}$.

Molecules present in solutions or in vitro biological samples which show cross-reactivity towards the antibodies of the present invention can be detected by immunoassays incorporating said antibodies.

The invention also describes an immunoassay method of detecting or determining 3,4-dichloro-N-[(1-(dimethylamino)cyclohexyl)methyl]benzamide and 3,4-dichloro-N-[(1-(methylamino)cyclohexyl)methyl]benzamide in a solution or an in vitro sample taken from an individual using one or more detecting agents and an antibody of the invention; and deducing the presence of, or amount of, 3,4-dichloro-N-[(1-(dimethylamino)cyclohexyl)-methyl]benzamide and 3,4-dichloro-N-[(1-(methylamino)cyclohexyl)methyl]benzamide. In a preferred embodiment, the antibody used in the method is derived from an immunogen of the invention.

By 'detecting' is meant qualitatively analysing for the presence or absence of a substance; by 'determining' is meant quantitatively analysing for the amount of substance present. It is common practice that in the immunoassay method the presence or amount of target analyte(s) (in the current instance 3,4-dichloro-N-[(1-(dimethylamino)cyclohexyl)-methyl]benzamide and 3,4-dichloro-N-[(1-(methylamino)cyclohexyl)methyl]benzamide) is gauged by reference to one or more calibrator values usually in the form of a cut-off value or calibration curve; the Immunoassay Development section herein describes the use of a calibrator to construct a calibration curve or 'standard curve' which allows the sensitivity (in this case the $IC_{50}$) and cross-reactivity of antibodies to the target analytes to be derived. However, it is possible that detection of the signal originating from the detecting agent does not make use of a calibrator—this possibility applies to the method of the invention.

A calibrator is well known in the art and refers to a reference value or values, the reference being a substance which enables a threshold concentration or the exact or calibrator equivalent amount of analyte(s) to be determined. The determination of an exact or calibrator equivalent amount of analyte(s) usually requires the construction of a calibration curve (also known as a standard curve). The number of calibrator points can vary, but is usually from 5 to 9. To enable a practical assay for clinical/commercial use, the binding of the antibody to the analyte(s) must be such that the concentration at which the analytes are detected or determined is at an acceptable level. The detecting agent (also known as a tracer or conjugate) is the substance which emits a detectable signal and comprises a moiety of similar structure to a target analyte conjugated, by way of a cross-linker, to a labelling agent, that is able to bind to one of the antibodies of the invention.

In one embodiment, the presence of detecting agent linked to the antibody can be detected or determined in between about 10 hours and about 1 minute, between about 2 hours and about 10 minutes, between about 1 and a half hours and about ten minutes, or between about 1 hour and 20 minutes. In yet another embodiment, the presence of detecting agent linked to the antibody can be detected or determined within about 30 minutes.

The term "subject" refers to an animal (e.g., a bird such as a chicken, quail or turkey, or a mammal), specifically a "mammal" including a non-primate (e.g., a cow, pig, horse, sheep, rabbit, guinea pig, rat, cat, dog, and mouse) and a primate (e.g., a monkey, chimpanzee and a human), and more specifically a human. In one embodiment, the subject is a non-human animal such as a farm animal (e.g., a horse, cow, pig or sheep), or a pet (e.g., a dog, cat, guinea pig or rabbit). In another embodiment, the subject is a "human".

The term "biological sample", as used herein, includes, without limitation, cell cultures or extracts thereof; biopsied material obtained from a mammal or extracts thereof; blood, saliva, urine, faeces, semen, tears, or other body fluids or extracts thereof. In one embodiment, the biological sample is a peripheral biological fluid, but is including whole blood, serum, plasma, hair or urine. The sample may also be a solution which is suspected of containing a drug. An in vitro sample is any suitable biological sample such as, but not limited to, blood, serum, plasma, urine or saliva. The in vitro sample is preferably a serum, plasma or urine sample. The solution can be a liquid suspected of containing one or more of these drugs. Alternatively, as these drugs can be in tablet or plant form e.g. sold as a herbal product, analysis of drugs suspected of containing these psychoactive ingredients may require pre-treatment to achieve a formulation suitable for analysis, such as dissolution in a suitable liquid.

The immunoassay method is most suited to the competitive assay format in which a target analyte which binds to the antibody i.e. the molecule to be detected or determined, competes with a detecting agent (also called a 'tracer' or 'conjugate') which also binds to the antibody, for binding sites on the antibody; the more analyte present the less detecting agent that binds to the antibody and the lower the measured signal. The detecting agent can be a substance such as an enzyme, a substance having fluorescent properties or a radioactive label; it is usual for an immunoassay that the detecting agent is a structure similar to the target analyte in which an enzyme or a substance having fluorescent properties has been conjugated, or in which a radiolabel has been incorporated. The "detecting agent" can be conjugated to a labelling agent. The labelling agent is selected from an enzyme, a luminescent substance, a radioactive substance, or a mixture thereof. In one embodiment, the labelling agent is an enzyme, for example a peroxidase, most specifically horseradish peroxidase (HRP). Alternatively, or additionally, the labelling agent is a luminescent substance which may be a bioluminescent, chemiluminescent or a fluorescent material. Conjugation is by way of standard methods familiar to the skilled person. Typically enzymes promote light emission from substrates added to the assay medium. The 'detecting and determining' criteria for the immunoassay method includes, as is well-known in the art, detection of a signal, exceeding a pre-defined cut-off/concentration value or measuring the calibrator equivalent value as derived from a calibrator curve (also referred to as a standard curve).

In relation to the antibodies described herein, in the context of the current invention, 'from which they are raised' is synonymous with 'to which they are derived'.

Due to inter-molecular attractive forces such as hydrogen bonding and van der Waal's forces, there is often a degree of binding or affinity between two molecules whatever their respective structures; the skilled person recognizes that no cross-reactivity or minimal cross-reactivity implies that in the context of a working immunoassay any binding or interaction between an antibody and non-target analytes is at such a low level that it does not compromise the integrity of the immunoassay i.e. false positives are avoided. The antibodies of the invention, separate of or as part of the immunoassay method described, do not display cross-reactivity to any compounds which could undermine the immunoassay method.

The invention further describes a substrate with which the antibodies of the invention engage. The antibodies can engage with the substrate by, for example, passive adsorption or can be chemically bonded to the substrate attached by way of, for example, covalent bonds. Such covalent bonding generally requires the initial introduction of a chemically active compound covalently attached to the substrate surface prior to antibody addition. The antibody itself may also require the addition of a chemical activating group to achieve substrate bonding. These requirements are well known in the art. The substrate can be any medium capable of adsorbing or bonding to an antibody, for example a bead or nanoparticle (optionally chemically-activated), but is preferably of a planar conformation (optionally chemically-activated) such as a microtitre plate or biochip. A biochip is a thin, wafer-like substrate with a planar surface which can be made of any suitable material such as glass or plastic but is preferably made of ceramic. The biochip is able to be chemically-activated prior to antibody bonding or is amenable to the passive adsorption of antibodies. The skilled person in biochip development for immunoassay application will recognize that a planar surface at high resolution e.g. if using a scanning electron microscope, is not perfectly 'flat' but will possess an uneven surface, the important aspect being that the 'approximately' planar surface is suitable for application. A microlayer coating of material can optionally be added to the planar surface of the substrate prior to antibody placement. Either the upper surface or both surfaces of the substrate can be coated. Other compound-specific or compound generic antibodies to other drugs of abuse can also be incorporated onto the substrate, such as antibodies cross-reactive to synthetic cannabinoids, LSD, salvinorin, ketamine, mephedrone methamphetamine, amphetamine and MDMA.

The invention further describes a kit comprising an antibody of the invention. The antibody is preferably attached to a microtitre plate or biochip; the kit can also incorporate a tracer and any further reagents necessary to enable a detectable or measurable signal to be produced. The chip can be integrated into or placed into a device with walls. Such a walled device can aid in the retention of added sample or solution.

Therefore, another aspect of the invention is a solid state device, preferably a biochip which is preferably ceramic, which supports an antibody of the invention. The solid state device can also support other antibodies which have a binding specificity which is different from the binding specificity of the antibodies of the invention. Such a support with multiple different antibodies is often described as a multianalyte array (Reference to an 'array' includes a microarray). If the method of detection is different fluorescent labels, each different fluorescent label emitting electromagnetic radiation at a unique wavelength, then the location of placement of the antibodies on the solid substrate is not critical. However, for antibodies forming part of a multi-analyte array in which the detectable label is, for example, a chemiluminescent molecule, the antibodies of differing specificity must not overlap and must be located in discrete areas on the solid state device. Such a system is also referred to as a spatially addressable multianalyte array.

Enzyme Immunoassays, ELISAs

The enzyme-linked immunosorbent assay (ELISA) is a test that uses antibodies and colour change to identify a substance.

Antigens from the sample are attached to a surface. Then, a further specific antibody is applied over the surface so it can bind to the antigen. This antibody is linked to an enzyme, and, in the final step, a substance containing the enzyme's substrate is added. The subsequent reaction produces a detectable signal, most commonly a colour change in the substrate.

Performing an ELISA involves at least one antibody with specificity for a particular antigen. The sample with an unknown amount of antigen is immobilized on a solid support (usually a polystyrene microtiter plate) either non-specifically (via adsorption to the surface) or specifically (via capture by another antibody specific to the same antigen, in a "sandwich" ELISA). After the antigen is immobilized, the detection antibody is added, forming a complex with the antigen. The detection antibody can be covalently linked to an enzyme, or can itself be detected by a secondary antibody that is linked to an enzyme through bioconjugation. Between each step, the plate is typically washed to remove any proteins or antibodies that are not specifically bound. After the final wash step, the plate is developed by adding an enzymatic substrate to produce a visible signal, which indicates the quantity of antigen in the sample.

Lateral Flow Devices

In recent years, the in vitro diagnostics industry has made enormous efforts to develop immunochromatographic tests. Such tests have found applications in both clinical and non-clinical fields. A clinical utility of this test format is particularly suited to point of care utilities.

Rapid immunochromatographic test devices, e.g. in the form of a test strip, are made up of a number of components. Such a test strip commonly includes a sample pad, a conjugate pad, a membrane, e.g. a nitrocellulose membrane, and an absorbent pad. The membrane is usually attached by means of an adhesive to a supporting backing, e.g. made of plastic. In practice, the user dispenses a patient sample (such as urine or whole blood) onto the sample pad. The sample then flows through the sample pad into the conjugate pad, where it mixes with, and releases, the detector reagent. This mixture then flows across the membrane, where it binds with the test and control reagents located in the capture test zone (sample zone) and negative control zone, respectively. When the mixture binds to the reagent that forms the test line, a positive result is indicated. The colour intensity of the test line is proportional to the concentration of analyte in the sample. Excess sample that flows beyond the test and control zones is taken up in the absorbent pad.

Rapid immunochromatographic test devices for diagnostic purposes are easy to operate and thus do not only contribute to the comfort of professional users, e.g. medical stuff, but also allow the operation by non-professionals users, e.g. most patients.

Biochips

Biochips are components used for example in chemical analysis (including Proteomic and Molecular analysis) either to host a test reaction and/or to supply samples under test or reagents. Generally, a Biochip comprises a solid substrate, on which is arranged one or more test sites at which a reaction can take place in use. For instance, the test site may carry one or more reagents (e.g. ligands such as antibodies or antigens) adsorbed to the substrate, which are activated by the addition of a sample substance (e.g. analytes present in the sample bind to specific ligands). Such chips are sometimes referred to as a "lab on a chip" and can also incorporate tools for controlling steps of a reaction. As an example, one Biochip supplied by Randox Laboratories Limited (55 Diamond Road, Crumlin, County Antrim, United Kingdom, BT29 4QY) is used as a medium for performing multiplex analysis of biological samples using a chemiluminescence method. In this example, the Biochip takes the form of a small ceramic chip with a specialised surface preparation which is sensitive to environmental degradation. Therefore the Biochip is generally delivered in an environmentally sealed format, usually evacuated, sealed foil bags.

For instance, the Evidence™ analyser by Randox Laboratories Ltd uses biochips which are fitted into a plastic holder defining three recesses arranged in a line. Each recess is approximately square and sized to just accommodate a biochip, which is also square, with a small clearance to allow the chip to be placed. The "strip" of three mounted biochips is placed within a sealed foil bag for storage, which is then opened when the biochips are required for use. The plastic holder may be placed on a carrier alongside two further strips of three biochips to form a 3×3 array of biochips. The carrier has a keying feature for engagement with a robotic arm such that the array can be transported within the analyser via robotic handling. This configuration is useful for batch analysis.

A "Biochip" is a general term for a reaction platform for hosting chemical, biochemical, proteomic or molecular tests, as may be required for medical diagnosis, drug detection, etc. Typically, a Biochip comprises an inert substrate, such as silicon or glass (often of the order of about 1 $cm^2$ or less in surface area), on which one or a plurality of reaction sites is provided. The sites generally carry one or more ligands, for example, one or more antibodies, selected for the test (or "assay") to be performed, adsorbed to the surface of the chip for activation upon combination with a sample applied to the chip (e.g. a blood sample) and/or a reagent. The reactions can be detected using a number of alternative techniques, including detection of chemiluminescence generated by the reaction. Some biochips carry a very large number (hundreds or thousands) of such tests sites, typically arranged in a grid or array, making it possible to carry out numerous assays simultaneously, and using the same single specimen.

General Methods, Examples and Results

Haptens, Crosslinkers, Immunogens and Detecting Agents

In immunology, haptens (can be referred to as 'small molecules') are defined as chemicals which by themselves cannot elicit immune responses; they require chemical coupling to larger immunogenic molecules (the accm), to be capable of inducing an immune response. As stated, accms are well known in the art and can be any material that makes all or part of the hapten immunogenic. The process of immunogen formation generally involves coupling of the hapten to a crosslinking agent, the latter subsequently coupled to an accm. Alternatively, the crosslinker can be attached to the accm, followed by conjugation of hapten. It is also possible to couple a hapten directly to the accm. The concept of accm-(crosslinker)$_n$-hapten conjugation to form an immunogen, where n=0 or 1, is well-established; the conjugation and exact point of attachment of a hapten to a crosslinker must be adapted to the particular hapten and is guided by synthetic organic chemistry and immunology principles. Numerous crosslinkers and accms are commercially available and have been described in the literature (Thermo Scientific Crosslinking Technical Handbook, 1606073 04/2009; Bioconjugate Techniques G. Hermanson, ed, Academic Press, 1996, 785 pp—lists common carrier proteins). An example of a crosslinking group is 4-N-maleimidomethylcyclohexyl-1-carboxylic acid NHS ester solution (available from Sigma-Aldrich catalogue number 5525). An alternative crosslinker which can used to couple to haptens possessing a carboxylic acid is EDC and sulfo-NHS both of which are known in the art and are commercially available. In order to confirm that adequate conjugation of hapten to carrier material has been achieved, prior to immunisation, each immunogen is evaluated using matrix-assisted UV laser desorption/ionisation time-of-flight mass spectroscopy (MALDI-TOF MS).

The haptens can also be coupled to a detectable labelling agent such as an enzyme (for example, horseradish peroxidase), a substance having fluorescent properties or a radioactive label for the preparation of detecting agents for use in the immunoassays. The fluorescent substance may be, for example, a monovalent residue of fluorescein or a derivative thereof.

General Procedure for MALDI-TOF Analysis of Immunogens

MALDI-TOF mass spectrometry was performed using a Voyager STR Biospectrometry Research Station laser-desorption mass spectrometer coupled with delayed extraction. An aliquot of each sample to be analysed was diluted in 0.1% aqueous trifluoroacetic acid (TFA) to create 1 mg/mL sample solutions. Aliquots (1 µl) were analysed using a matrix of sinapinic acid and bovine serum albumin (Fluka) was used as an external calibrant.

Preparation of Antisera

In order to generate polyclonal antisera, an immunogen of the present invention is mixed with Freund's adjuvant and the mixture is injected into a host animal, such as rabbit, sheep, mouse, guinea pig or horse. Sheep are the preferred host animal. Further injections (boosts) are made and serum is sampled for evaluation of the antibody titre. When the optimal titre has been attained, the host animal is bled to yield a suitable volume of specific antiserum. The degree of antibody purification required depends on the intended application. For many purposes, there is no requirement for purification, however, in other cases, such as where the antibody is to be immobilised on a solid support, purification steps can be taken to remove undesired material and eliminate non-specific binding. In one embodiment, the purification is by immunoglobulin precipitation, antigen-specific affinity purification, column chromatography, such as, size-exclusion chromatography or ion exchange chromatography.

Immunoassay Development

The process of developing an immunoassay is well known to the person skilled in the art. Briefly, for a competitive immunoassay in which the target analyte is a non-immunogenic molecule such as a hapten, the following process is conducted: antibodies are produced by immunising an animal, preferably a mammalian animal, by repeated administration of an immunogen. The serum from the immunised animal is collected when the antibody titre is sufficiently high. A detecting agent is added to a sample containing the target analyte and the raised antibodies, and the detecting agent and analyte compete for binding to the antibodies. The process may comprise fixing said serum antibodies to a backing substrate such as a polystyrene solid support or a ceramic chip. The antibodies can be polyclonal or monoclonal using standard techniques. The signal emitted in the immunoassay is proportionate to the amount of detecting agent bound to the antibodies which in turn is inversely proportionate to the analyte concentration. The signal can be detected or quantified by comparison with a calibrator.

Scheme I below depicts the reaction described in Example 1.

Scheme I

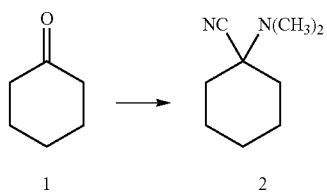

Reagents and conditions: NH(CH$_3$)$_2$ HCl, KCN, H$_2$O, rt.

Example 1

Synthesis of 1-cyano-1-cyclohexyldimethylamine (2): Dimethylammonium chloride (40.75 g, 0.5 mol) dissolved in water (100 mL) was added cyclohexanone (1) (49.0 g, 0.5 mol), quickly followed by a solution of potassium cyanide (34.0 g, 0.5225 mol) added over a period of five minutes. The reaction mixture was stirred at room temperature for 24 hours during which time a colourless crystalline solid was formed. The solid was filtered off, washed with ice cold water (200 mL), dissolved in benzene (150 mL) and rewashed with water (100 mL). The aqueous layer was extracted with benzene (100 mL), the benzene solutions then being combined, dried over sodium sulphate and evaporated under reduced pressure. The oily residue (57.0 g) solidified to give 1-Cyano-1-cyclohexyldimethylamine (2).

Scheme II below depicts the reaction described in Example 2.

Scheme II

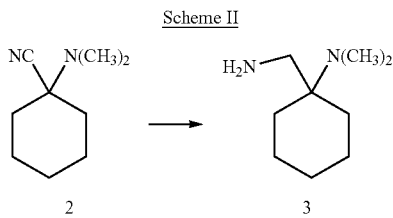

Reagents and conditions: LiAlH$_4$, Et$_2$O, rt.

Example 2

Synthesis of 1-aminomethyl-1-cyclohexyldimethylamine (3): 1-Cyano-1-cyclohexyldimethylamine (2) (22.7 g, 0.15 mol) was dissolved in dry ether (200 mL) and added dropwise to a stirred suspension of lithium aluminium hydride (11.37 g, 0.3 mol) in dry ether (300 mL). The suspension was stirred overnight at room temperature and excess lithium aluminium hydride decomposed by dropwise addition of water (28 mL) and 30% sodium hydroxide solution (21 mL) followed by water (50 mL). The ether layer was separated, dried over sodium sulphate, filtered and evaporated to dryness to yield a colourless, mobile oil (21.4 g, 92.5%) of the free base of 1-aminomethyl-1-cyclohexyldimethylamine (3).

Scheme III below depicts the reaction described in Example 3.

Scheme III

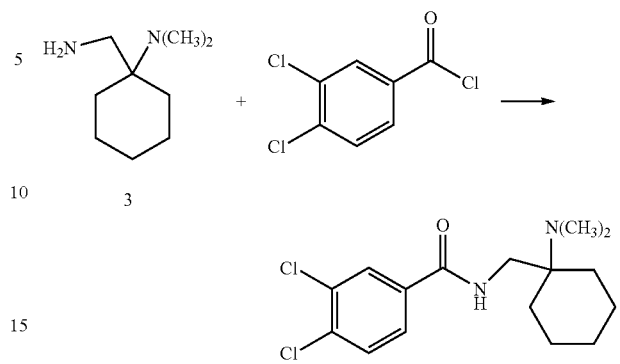

Reagents and conditions: TEA, THF 0° C. to rt

Example 3

Synthesis of 1-(3,4-dichlorobenzamidomethyl)-cyclohexyldimethylamine (AH-7921) (4): To a cooled solution mixture at 0° C. of 1-aminomethyl-1-cyclohexyldimethylamine (3) (16.96 g, 0109 mol) and TEA (16.0 ml, 0.115 mol) in anhydrous THF (50 mL) was added dropwise over a period of 1 hour a solution of 3,4-Dichlorobenzoyl chloride (23.44 g, 0.112 mol) in anhydrous THF (100 mL) and the mixture was left stirring at room temperature for 2 hours. Water (200 mL) and ethyl acetate (200 mL) were added to the mixture, the organic phase was separated and the aqueous was extracted by ethyl acetate (2×200 mL). The combined organic layers were dried over sodium sulphate, filtered and evaporated to dryness. Recrystallisation of the crude product from boiling ethyl acetate yield (30.65 g) of 1-(3,4-dichlorobenzamidomethyl)-cyclohexyldimethylamine (AH-7921) (free base) (4).

Scheme IV below depicts the reaction described in Example 4.

Scheme IV

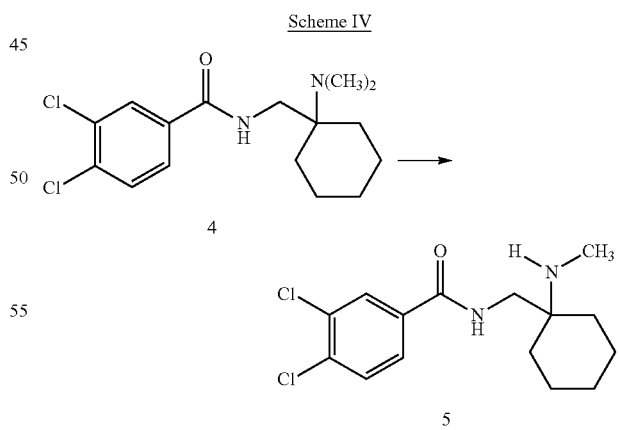

Reagents and conditions: DEAD, toluene; 55° C., 18 hr.

Example 4

Synthesis of 1-(3,4-dichlorobenzamidomethyl)-cyclohexylmethylamine (nor-AH-7921) (5): To a solution of 1-(3,4- dichlorobenzamidomethyl)-cyclohexyldimethylamine (AH-7921) (4) (10.0 g, 0.03 mol) in toluene (100 mL) was added DEAD (6.1 ml, 0.039 mol) and the mixture was heated at 55° C. for 18 hours. The mixture was evaporated to dryness and the crude mixture obtained was diluted with ethanol (70 mL) and saturated ammonium chloride solution (70 mL) and heated at reflux for 3 hours. The mixture was concentrated to dryness. The residue obtained was dissolved in 10% potassium carbonate solution (50 mL) and water (150 mL). The mixture was than extracted with ethyl acetate (3×200 mL). The combined organic layers were dried over sodium sulphate, filtered and evaporated to dryness to give crude yellow oil. The product was purified by chromatography (Biotage Isolera, SNAP 340 g ultra cartridge-1% methanol/chloroform; 7% methanol/chloroform and 40% methanol/chloroform) to yield the 1-(3,4-dichlorobenzamidomethyl)-cyclohexylmethylamine (nor-AH-7921) (5) (6.3 g) as colourless oil which solidified overtime on cooling.

Scheme V below depicts the reaction described in Example 5.

Scheme V

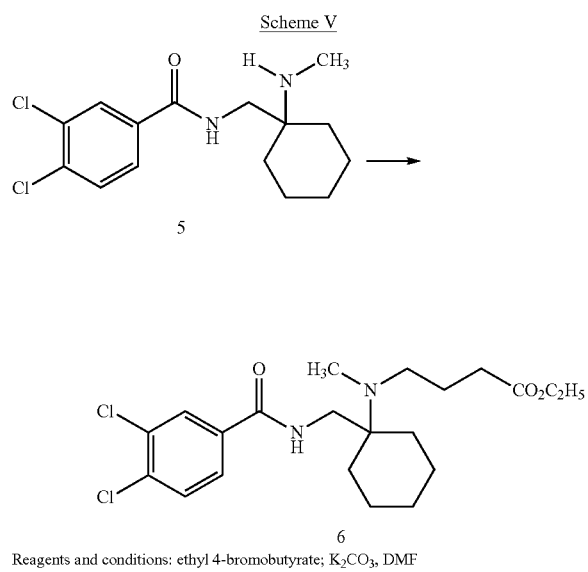

Reagents and conditions: ethyl 4-bromobutyrate; K₂CO₃, DMF

Example 5

Synthesis of N-(4-ethoxy-4-oxobutyl)-nor-AH-7921 (6): To a mixture of 1-(3,4-Dichlorobenzamidomethyl)-cyclohexylmethylamine (nor-AH-7921) (5) (3.15 g, 0.01 mol) in DMF (100 mL) and potassium carbonate (3.45 g, 0.025 mol) was added Ethyl 4-bromobutyrate (3.9 g, 0.02 mol), the mixture was than heated at 70° C. and stirred overnight. The solvent was removed under vacuum, water (100 mL) was added and the mixture extracted with ethyl acetate (2×100 mL). The combined ethyl acetate layers were washed by water (50 mL), brine (50 ml), dried over sodium sulphate, filtered and concentrated to dryness. The crude product obtained was purified by column chromatography (40% ethyl acetate/hexane, Biotage Isolera) to yield the N-(4-ethoxy-4-oxobutyl)-nor-AH-7921 (6) as a clear oil (6.0 g).

Scheme VI below depicts the reaction described in Example 6.

Scheme VI

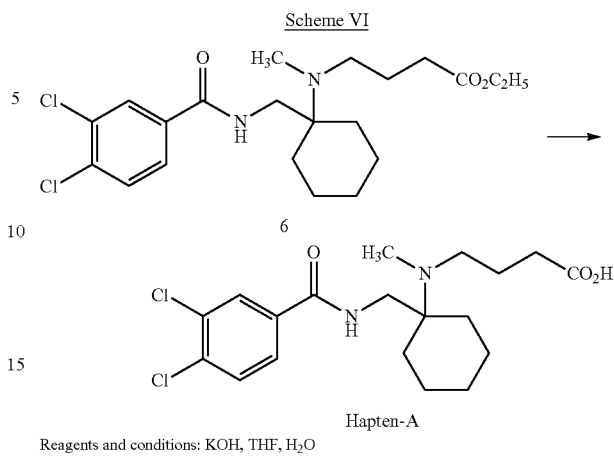

Reagents and conditions: KOH, THF, H₂O

Example 6

Synthesis N-(carboxypropyl)-nor-AH-7921 (Hapten-A): To a solution of N-(4-ethoxy-4-oxobutyl)-nor-AH-7921 (6) (2.9 g, 6.75 mmol) in a mixture of THF (30 mL)/water (30 mL)/methanol (10 mL) was added KOH (1.4 g, 25 mmol) and the mixture was stirred at room temperature overnight. TLC showed complete reaction. The mixture was evaporated to dryness, water (100 mL) was added and the aqueous solution washed by diethyl ether (100 mL). The aqueous solution was acidified with hydrochloric acid (6N) to pH 4 and extracted first with dichloromethane (3×120 mL). The combined dichloromethane extracts were washed by water (60 mL), brine (100 mL), dried over sodium sulphate, filtered and evaporated to dryness. Purification by column chromatography (Biotage, Isolera, SNAD 25 g cartridge) using 30% methanol/chloroform yielded N-(carboxypropyl)-nor-AH-7921 (Hapten-A) (1.75 g) as a white foamy solid. $^{13}$C NMR (CD$_3$OD): δ 177.4, 169.6, 137.3, 134.9, 133.8, 131, 130.9, 128.6, 70.2, 58.3, 52.2, 40.4, 35.0, 32.9, 29.9, 25.5, 23.2, 22.2 and 18.3.

Example 7

Conjugation of N-(carboxypropyl)-nor-AH-7921 (Hapten-A) to BSA (Immunogen-1): To a solution of N-(carboxypropyl)-nor-AH-7921 (Hapten-A) (15.4 mg) in DMF (0.5 mL) was added N-(3-dimethylaminopropyl)-N'-ethylcarbodiimide hydrochloride (EDC. HCl) (36.9 mg) and N-hydroxysuccinimide (22.1 mg) and the mixture was incubated on the roller at room temperature overnight. This solution was added dropwise to a solution of BSA (50 mg, 0.75 micomol) in phosphate buffer saline (50 mM) (pH 8.0) (5 mL). The resulting solution was incubated on the roller at room temperature overnight. Excess hapten was removed by dialysis against phosphate buffer saline, pH 7.2 (3 changes) for 24 hours at 4° C., and freeze-dried. MALDI results showed 26.5 molecules of N-(carboxypropyl)-nor-AH-7921 (Hapten-A) had been conjugated to one molecule of BSA.

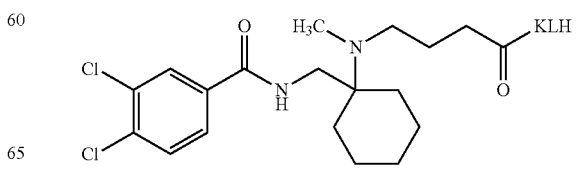

N-(carboxypropyl)-nor-AH-7921-KLH Immunogen 2

Example 8

Conjugation of N-(carboxypropyl)-nor-AH-7921 (Hapten-A) to KLH (Immunogen-2): To a solution of N-(carboxypropyl)-nor-AH-7921 (Hapten-A) (30.9 mg) in DMF (1.0 mL) was added N-(3-dimethylaminopropyl)-N'-ethyl-carbodiimide hydrochloride EDC.HCl (73.7 mg) and N-hydroxysuccinimide (44.3 mg) and the mixture was incubated on the roller at room temperature overnight. This solution was added dropwise to a solution of KLH (100 mg) in phosphate buffer saline (50 mM) (pH 8.0) (10 mL). The resulting solution was incubated on the roller at room temperature overnight. Excess hapten was removed by dialysis against phosphate buffer saline, pH 7.2 (3 changes) for 24 hours at 4° C., and freeze-dried.

Example 9

Conjugation of N-(carboxypropyl)-nor-AH-7921 (Hapten-A) to HRP (Tracer-1): EDC hydrochloride (1.5 mg) was dissolved in water (0.5 mL) and immediately added to a solution of N-(carboxypropyl)-nor-AH-7921 (Hapten-A) (3.0 mg) in DMF (0.2 mL). After mixing, this solution was added dropwise to a solution of HRP (20 mg) in water (1 mL). N-hydroxysuccinimide (1 mg) was added and the reaction mixture was incubated in the dark at room temperature overnight. Excess hapten was removed with double PD-10 columns (Pharmacia) in series, pre-equilibrated with PBS at pH 7.2. The hapten-1-HRP conjugate (tracer-1) was then dialysed overnignt against 10 L of PBS at pH 7.2 at 4° C.

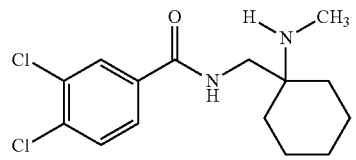 [SMILES: CNC1(CNC(=O)c2ccc(Cl)c(Cl)c2)CCCCC1]

3,4 Dichloro-N-[1-(methylamino)cyclohexylmethyl]benzamide (Nor-AH-7921)

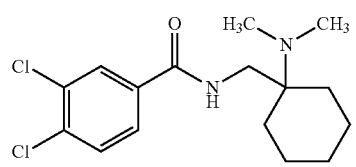 [SMILES: CN(C)C1(CNC(=O)c2ccc(Cl)c(Cl)c2)CCCCC1]

3,4 Dichloro-N-[1-(dimethylamino)cyclohexylmethyl]benzamide (AH-7921)

Preparation of Antisera

Pre-immunization blood samples are collected from young adult, female, Texel sheep. Texel sheep is a breed of domestic sheep originally from the island of Texel in the Netherlands. In order to generate polyclonal antisera, 2 mg of Immunogen-2 is prepared in PBS, mixed at a ratio of 50% immunogen in PBS to 50% Freund's Complete adjuvant (Sigma, Product Number F5881) and emulsified by repeatedly passing the mixture through a tip on the end of a 1 mL syringe, until it reaches the required semi-solid consistency. 1 mL of the emulsified mixture is injected intramuscularly into each host animal (sheep) as the primary immunisation dose. Further injections (boosts) are prepared (1 mg of immunogen is prepared in PBS and mixed at a ratio of 50% Immunogen in PBS/50% Freunds Incomplete adjuvant, Sigma, Product Number—F5506). Boost injections are delivered intramuscularly at monthly intervals, 1 mL per animal. Serum is sampled monthly by collection of whole blood from the jugular vein for evaluation of the antibody titre. The degree of antibody purification required depends on the intended application. (For many purposes, there is no requirement for purification of the serum, however, in other cases, such as where the antibody is to be immobilised on a solid support, purification steps (such as caprylic acid/ammonium sulphate precipitation) can be taken to remove undesired material and eliminate non-specific binding.)

Caprylic Acid Purification Method 2 mL of antisera was diluted with 8 mL of 60 mM Sodium acetate buffer, pH 4.4 in a 30 mL universal tube. 200 µl of Caprylic acid was added slowly whilst shaking. The resulting mixture was rolled or shaken for 30 minutes at room temperature. The solution was centrifuged at 2000 rpm at 4° C. for 20 minutes. The supernatant was filtered through a 0.2 µm serum Acrodisc filter. 1.4 mL of 0.5M Carbonate-bicarbonate buffer, pH 10.7 was added and the solution was cooled to 4° C. 9 mL of saturated Ammonium sulphate solution was added slowly whilst shaking. The resulting mixture was rolled or shaken for 30 minutes at room temperature, and centrifuge at 2000 rpm at 4° C. for 35 minutes. The supernatant was poured off and the was re-suspended pellet in 2 mL of PBS, pH 7.2. It was dialysed overnight at 4° C. in PBS, pH 7.2, containing 0.09% Sodium azide. 30 Litres of PBS/Azide was used for a maximum of 80×2 mL cuts. It was filtered using a 0.2 µm serum Acrodisc filter and aliquot into 1.5 mL Eppendorf tubes.

Immunoassay Development

A detecting agent (hapten-A conjugated to HRP (Tracer-1)) is added to a sample containing the target analyte and the raised antibodies, promoting competition between the detecting agent and analyte for binding to the antibodies. The antibodies were contacted with a polystyrene solid support (e.g. dilution of antibodies in coating buffer and incubation at 37° C. for 2 hours to allow antibody binding to surface). The antibodies can be polyclonal or monoclonal using standard techniques, but the current invention makes use of polyclonal antibodies. The signal emitted in the immunoassay is proportionate to the amount of detecting agent bound to the antibodies which in turn is inversely proportionate to the analyte concentration. The signal can be detected or quantified by comparison with a calibrator which comprises known levels of target analyte.

Immunoassay

Antibodies were diluted in coating buffer and incubation at 37° C. for 2 hours to allow antibody binding to surface. The plate was washed. Detecting agent (hapten-A conjugated to HRP (Tracer-1)) was added to a sample containing the target analyte. The plate was washed. 125 µl of one-shot substrate (Thermo Fisher Product No. TMB005/001/UL—containing luminol) was added to each well and tapped gently. The plate was incubated at room temperature for 20 minutes in the dark. The reaction was stopped by addition of 125 µl of 0.2M Sulphuric acid to each well. The absorbance was measured at 450 nm using an ELISA plate reader (e.g. Biotek Elx800)

The cross-reactivity (CR) was calculated using the equation below. All calculations were based upon binding and displacement at the 50% of maximum OD (optical density) binding point. The maximum OD is the signal generated using tracer alone and 50% displacement (inhibition) corresponds to the $IC_{50}$.

$$\% \ CR \ of \ analyte \ Z = \left[\frac{IC_{50} \ of \ analyte \ with \ lowest \ IC_{50}^*}{IC_{50} \ of \ analyte \ Z}\right] \times 100$$

*analyte with lowest $IC_{50}$ is given a $CR$ of 100%.

The Table below discloses the Antibody binding characteristics of Antibody to AH-7921 and nor-AH-7921 (raised against Immunogen 2 of Example 8); and Tracer-1 of Example 9.

|  |  | AH-7921 Hydrochloride | | | Nor-AH-7921 | | |
|---|---|---|---|---|---|---|---|
| ng/ml |  | Ave OD | % CV | % B/B$_0$ | Ave OD | % CV | % B/B$_0$ |
| 0.000 | L1 | 1.620 | 5.0 | 100 | 1.599 | 1.7 | 100 |
| 0.156 | L2 | 0.509 | 4.7 | 31 | 0.576 | 1.3 | 36 |
| 0.313 | L3 | 0.284 | 1.1 | 18 | 0.380 | 1.1 | 24 |
| 0.625 | L4 | 0.157 | 1.6 | 10 | 0.247 | 1.1 | 15 |
| 1.250 | L5 | 0.082 | 0.7 | 5 | 0.164 | 4.9 | 10 |
| 2.500 | L6 | 0.045 | 3.8 | 3 | 0.103 | 3.4 | 6 |
| 5.000 | L7 | 0.025 | 2.3 | 2 | 0.072 | 3.0 | 4 |
| 10.000 | L8 | 0.015 | 4.9 | 1 | 0.045 | 4.4 | 3 |
|  | IC$_{50}$ |  | 0.081 |  |  | 0.086 | |
|  | % CR |  | 100.0% |  |  | 94.186 | |

Ave OD = average optical density
CV = coefficient of variation of OD
B = absorbance at 450 nm at x ng/mL standard concentration
B$_0$ = absorbance at 450 nm at 0 ng/mL standard concentration
IC$_{50}$ = standard concentration which produces 50% inhibition of maximal signal
B/B$_0$ = (B/B$_0$) × 100
CR = cross-reactivity The data of Table 1 details highly sensitive antibodies of $IC_{50} < 0.10$ ng/mL which bind to AH-7921 and nor-AH-7921.

What is claimed is:

1. A polyclonal antibody raised against an immunogen of the structure:

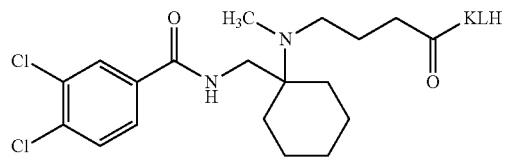

wherein the antibody binds to (i) 3,4-dichloro-N-[(1-(dimethylamino)cyclohexyl)methyl]benzamide and (ii) 3,4-dichloro-N-[(1-(methylamino)cyclohexyl)methyl]benzamide, and wherein the antibody has a relative cross-reactivity of 100% to 3,4-dichloro-N-[(1-(dimethylamino)cyclohexyl)methyl]benzamide and 94.186% to 3,4-dichloro-N-[(1-(methylamino)cyclohexyl)methyl]benzamide, wherein the cross-reactivity is measured in the presence of a detecting agent comprising N-(carboxypropyl)-3,4-dichloro-N-[1-(methylamino)cyclohexyl)methyl]benzamide conjugated to horseradish peroxidase.

2. The polyclonal antibody according to claim 1, which has been purified by immunoglobulin precipitation, antigen-specific affinity purification, size-exclusion chromatography or ion exchange chromatography.

3. The polyclonal antibody according to claim 1, wherein the antibody is adsorbed on or attached to a solid state device.

4. A method of detecting or determining 3,4-dichloro-N-[(1-(dimethylamino)cyclohexyl)methyl]benzamide or 3,4-dichloro-N-[(1-(methylamino)cyclohexyl)methyl]benzamide in a sample comprising:

i) contacting the sample with a detecting agent and the polyclonal antibody according to claim 1; and ii) detecting or determining the amount of the detecting agent bound to the polyclonal antibody.

5. The method according to claim 4, wherein the polyclonal antibody is adsorbed on or attached to a solid state device.

6. The method according to claim 4, wherein the detecting agent is conjugated to a labelling agent, and wherein the labelling agent is horseradish peroxidase (HRP).

7. The method according to claim 6, wherein the presence of the labelling agent is detected or determined by a colour change in response to reaction of the labelling agent with a substrate.

8. The method according to claim 7, wherein the colour change is detected or determined by reading the absorbance at 450 nm.

9. The method according to claim 4, wherein the presence of the detecting agent linked to the polyclonal antibody can be detected or determined in between about 2 hours and about 10 minutes.

10. A kit comprising the polyclonal antibody according to claim 1.

11. The kit according to claim 10, in which the polyclonal antibody is adsorbed on or attached to a solid state device.

* * * * *